(12) United States Patent
Matsumoto

(10) Patent No.: US 7,502,025 B2
(45) Date of Patent: Mar. 10, 2009

(54) IMAGE PROCESSING METHOD AND PROGRAM FOR VISUALIZATION OF TUBULAR TISSUE

(75) Inventor: Kazuhiko Matsumoto, Minato-ku (JP)

(73) Assignee: Ziosoft, Inc., Tokyo (JP)

(*) Notice: Subject to any disclaimer, the term of this patent is extended or adjusted under 35 U.S.C. 154(b) by 187 days.

(21) Appl. No.: 11/146,344

(22) Filed: Jun. 6, 2005

(65) Prior Publication Data
US 2006/0221074 A1    Oct. 5, 2006

(30) Foreign Application Priority Data
Sep. 2, 2004    (JP)    .............................. 2004-255670

(51) Int. Cl.
*G06T 17/00*    (2006.01)
(52) U.S. Cl. ..................................... 345/424
(58) Field of Classification Search .................. None
See application file for complete search history.

(56) References Cited

U.S. PATENT DOCUMENTS

| | | | | |
|---|---|---|---|---|
| 5,604,778 | A | * | 2/1997 | Polacin et al. .................. 378/9 |
| 5,782,762 | A | * | 7/1998 | Vining ......................... 600/407 |
| 5,953,013 | A | * | 9/1999 | Shimizu ....................... 345/419 |
| 6,252,599 | B1 | * | 6/2001 | Natsuko et al. ............. 345/419 |
| 6,456,735 | B1 | * | 9/2002 | Sato et al. .................... 382/131 |
| 6,461,298 | B1 | * | 10/2002 | Fenster et al. ............... 600/437 |
| 2002/0054662 | A1 | * | 5/2002 | Verdonck et al. ............. 378/62 |
| 2003/0152897 | A1 | * | 8/2003 | Geiger ........................ 434/262 |

FOREIGN PATENT DOCUMENTS

| | | |
|---|---|---|
| JP | 2004-529715 | 9/2004 |
| WO | 02-093496 | 11/2002 |

OTHER PUBLICATIONS

Mori, K., Hayashi, Y., Suenaga, Y., Toriwaki, J., Hasegawa J., Katada, K., A Method for Detecting Unobserved Regions in Virtual Endoscopy System, May 2001, Proceedings of SPIE, vol. 4321, pp. 134-145.*
Bartroli et al., "Virtual Colon Unfolding", 2001, pp. 411-420.
Japanese Office Action Dated Nov. 21, 2007.

* cited by examiner

*Primary Examiner*—Ulka Chauhan
*Assistant Examiner*—Said Broome
(74) *Attorney, Agent, or Firm*—Pearne & Gordon LLP

(57) ABSTRACT

A virtual ray makes one revolution around an imaginary path with an umbrella-like elevation angle θ kept constant with respect to the imaginary path to thereby generate a projected image. When the virtual ray is radiated obliquely, a shaded portion of an inner wall surface of a tubular tissue can be observed clearly.

23 Claims, 20 Drawing Sheets

UMBRELLA-SHAPED PROJECTION METHOD

FIG. 4A
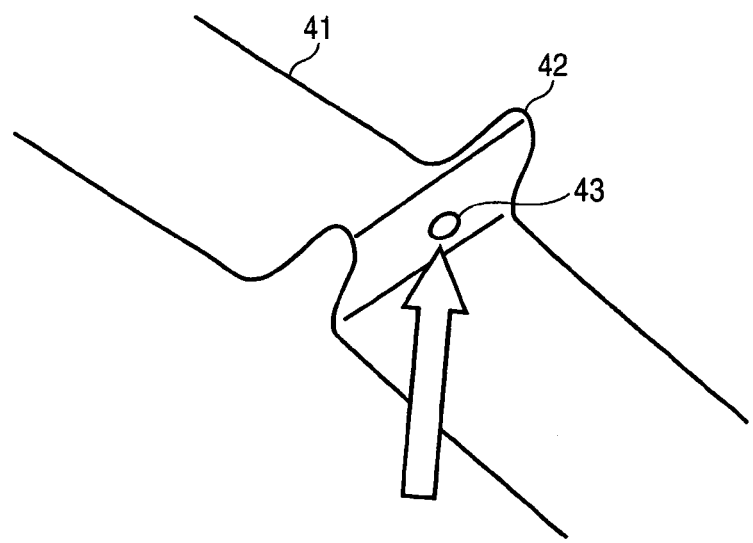
FIG. 4B  FIG. 4C  FIG. 4D
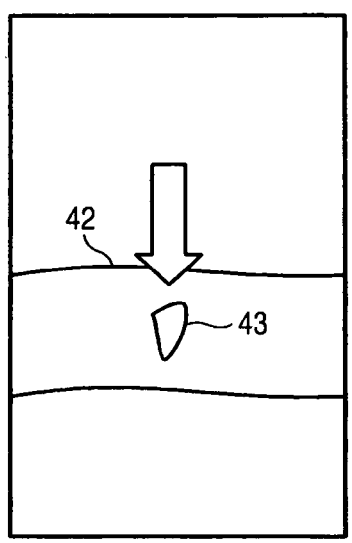 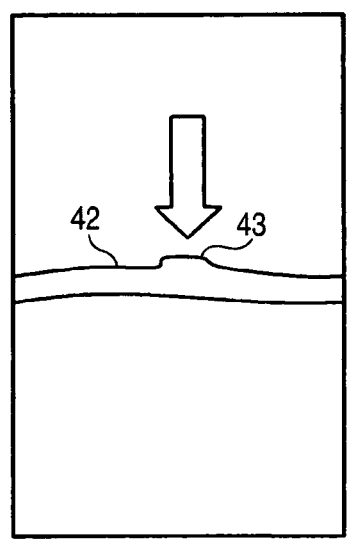 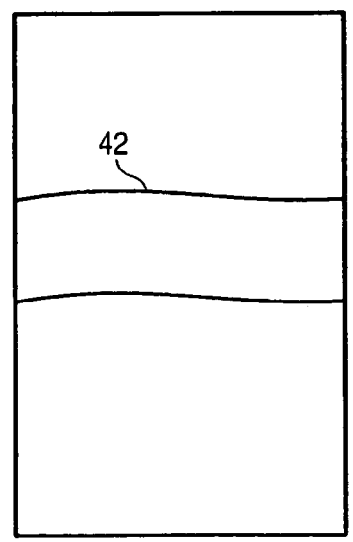
θ = 45°    θ = 90°    θ = 135°

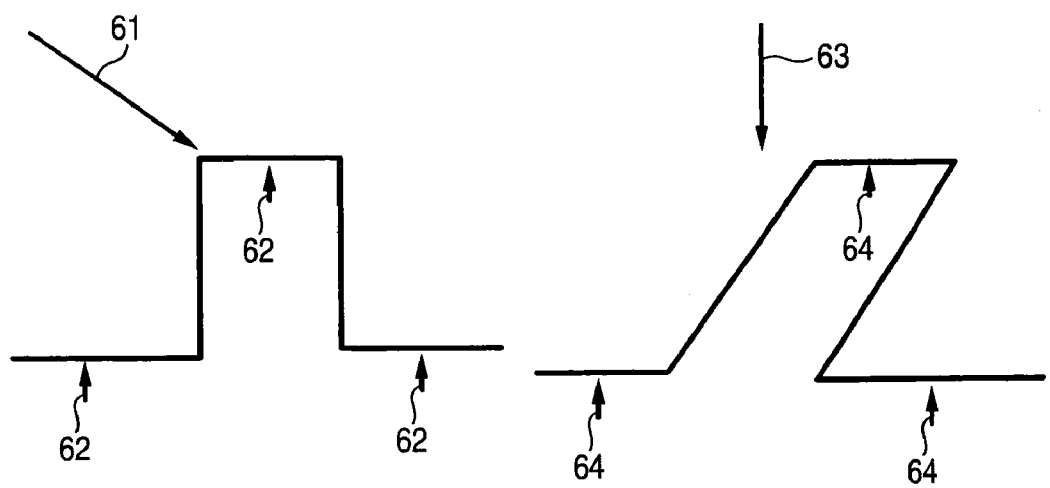
FIG. 6A
FIG. 6B
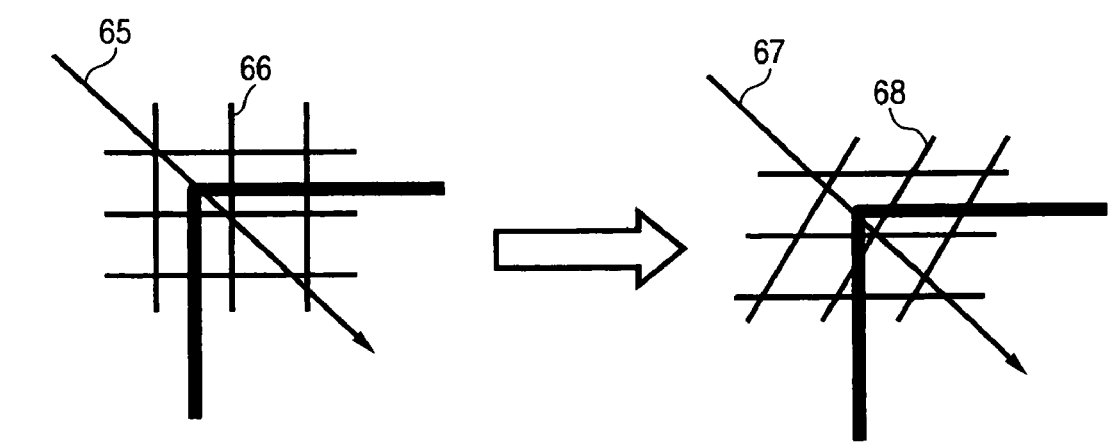
FIG. 6C

NONLINEAR RAY CASTING

NONLINEAR RAY CASTING

VORTEX RAY CASTING

VORTEX RAY CASTING

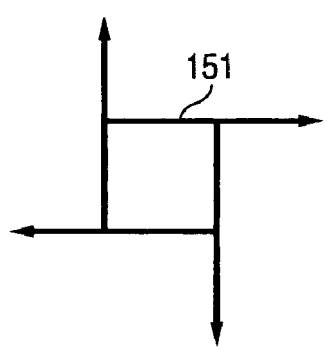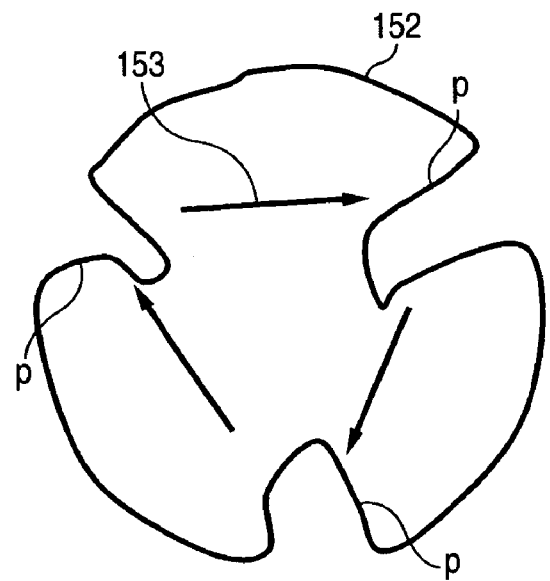
FIG. 9A
WINDMILL-SHAPED RAY CASTING
FIG. 9B
WINDMILL-SHAPED RAY CASTING

VISUALIZATION OF TUBULAR TISSUE

IMAGE OBTAINED BY VIRTUAL ENDOSCOPE

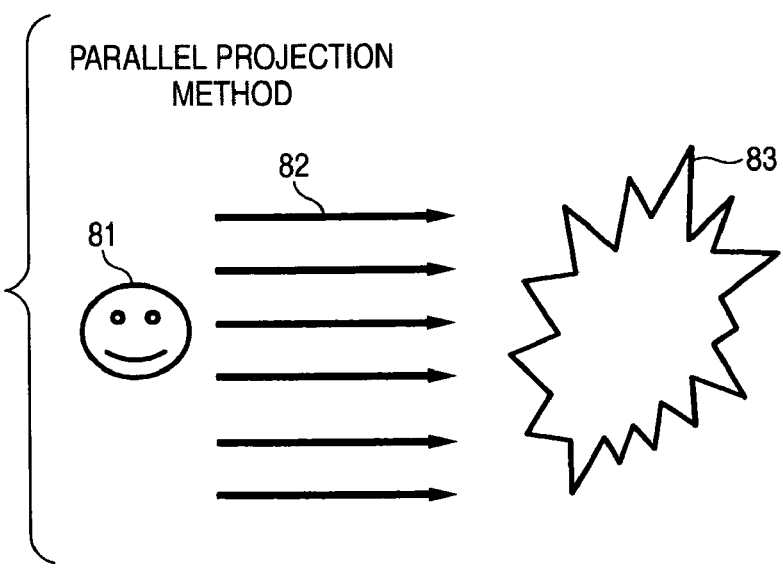
FIG. 13A PARALLEL PROJECTION METHOD
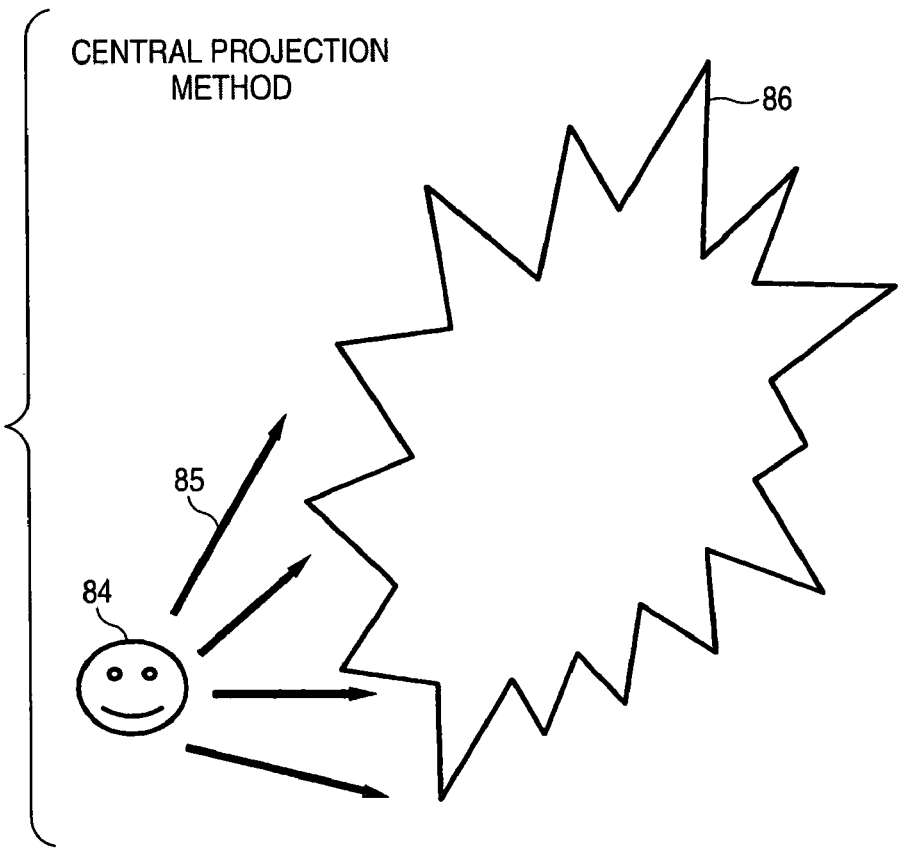
FIG. 13B CENTRAL PROJECTION METHOD I(u, v)

C(h, α)

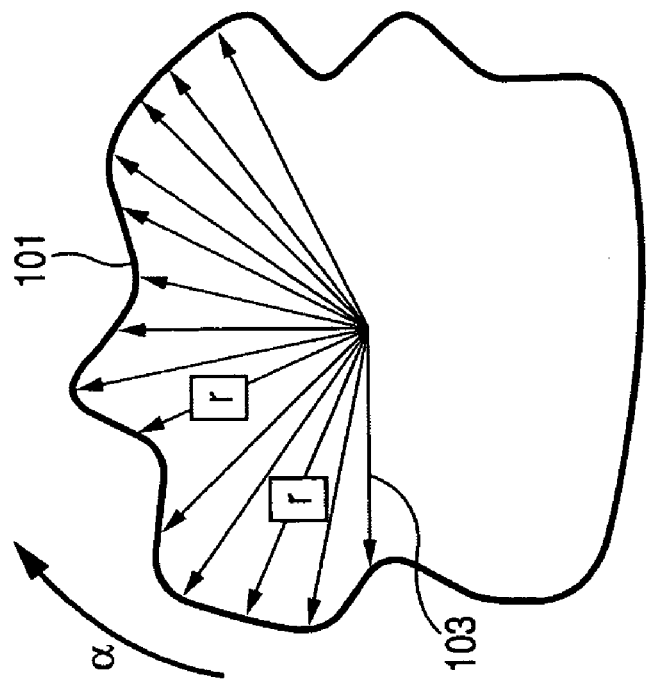
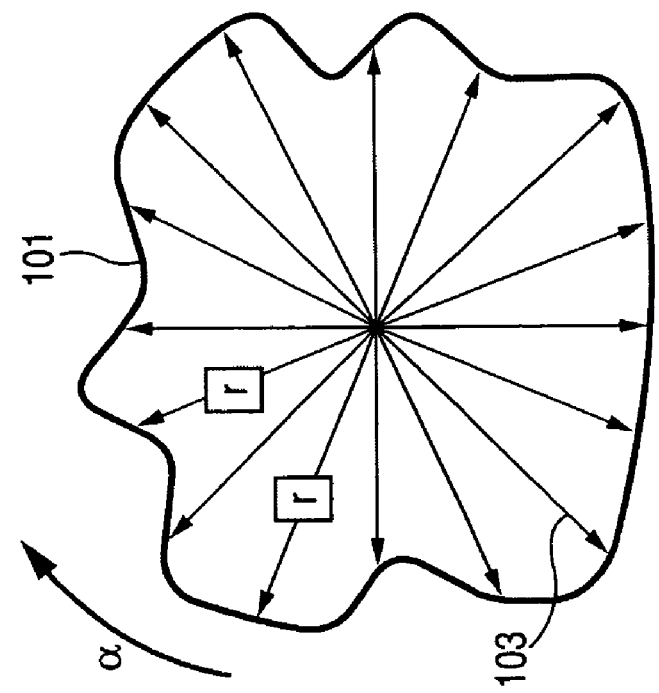

CURVED CYLINDRICAL PROJECTION METHOD

PROJECT FROM CENTER LINE

IMAGE PROCESSING METHOD AND PROGRAM FOR VISUALIZATION OF TUBULAR TISSUE

This application claims foreign priority based on Japanese Patent application No. 2004-255670, filed Sep. 2, 2004, the contents of which is incorporated herein by reference in its entirety.

BACKGROUND OF THE INVENTION

1. Field of the Invention

The present invention relates to an image processing method and an image processing program for visualizing a tubular tissue.

2. Description of the Related Art

A technique for visualizing the inside of a three-dimensional object has attracted public attention with the advance of image processing technology using a computer in recent years. Particularly in the medical field, medical diagnosis using a CT (Computed Tomography) apparatus or MRI (Magnetic Resonance Imaging) apparatus has been performed widely because a lesion can be detected early by visualizing the inside of a living body.

On the other hand, volume rendering is known as a method for obtaining a three-dimensional image of the inside of an object. In volume rendering, ray is emitted onto a three-dimensional voxel (micro volume element) space to thereby project an image on a projection plane. This operation is referred to as ray casing. In ray casting, a voxel value is acquired from a voxel at each sampling point which is sampled at a regular interval along the path of the ray.

The voxel is a unit for constituting a three-dimensional region of an object. The voxel value is a specific data expressing characteristic such as a density value of the voxel. The whole object is expressed by voxel data which is a three-dimensional arrangement of the voxel value. Generally, two-dimensional tomogram data obtained by CT is collected along a direction perpendicular to each sectional layer, and voxel data which is the three-dimensional arrangement of voxel value is obtained by performing necessary interpolation.

In ray casting, virtual reflected light of a virtual ray emitted onto an object from a virtual viewpoint is generated according to an opacity value artificially set for each voxel value. Then, the gradient of voxel data, that is, a normal vector is obtained to obtain a virtual surface, and a shading coefficient for shading is calculated from the cosine of an angle between the virtual ray and the normal vector. Virtual reflected light is calculated by multiplying the intensity of the virtual ray emitted on each voxel, the opacity value of the voxel and the shading coefficient.

FIG. 12A shows an example of a colon being displayed by a parallel projection method of volume rendering as an example of visualization of a tubular tissue in the inside of a human body. According to such volume rendering, a see-through image of the three-dimensional structure of the colon can be formed from two-dimensional tomogram data obtained successively along a direction perpendicular to sectional layers of the abdomen. The image obtained by the parallel projection method is suitable for observation from the outside but unsuitable for observation from the inside.

FIG. 12B shows an example of achieving an image obtained by a virtual endoscope by generating a centrally projected image of the inside of the colon with volume rendering. When voxel data is reconstructed from a viewpoint in the inside of the tubular tissue in this manner, inspection with an endoscope can be simulated. Accordingly, a polyp or the like in the inside of the tubular tissue can be detected.

However, the virtual endoscope image has a disadvantage that a large number of images obtained by the virtual endoscope has to be referred to perform diagnosis because the region allowed to be displayed at one time in each image obtained by the virtual endoscope is small.

FIGS. 13A and 13B are views for explaining a parallel projection method and a central projection method respectively. In the parallel projection method, as shown in FIG. 13A, virtual ray 82 is emitted parallel from a virtual viewpoint 81, and an image can be generated to observe an observation target 83 mainly from the outside. On the other hand, in the central projection method, as shown in FIG. 13B, virtual ray 85 is emitted radially from a virtual viewpoint 84. In the central projection method, an image with perspective and reality as the human sees an observation target 86 with his eyes can be generated.

FIGS. 14A and 14B show an example of display of an exfoliated image of a tubular tissue using a cylindrical coordinate system in ray casting. According to the central projection method shown in FIG. 13B, inspection of the colon or the like with an endoscope can be simulated, but it is difficult to understand the position or size of a polyp or the like in the wall of the tubular tissue accurately when the inside of the colon is inspected while scanned.

Therefore, as shown in FIG. 14A, a virtual viewpoint 91 is placed on a center line 94 of a colon 93. Virtual ray 92 is radiated from the virtual viewpoint 91 in directions perpendicular to the center line 94, and an image of the inner wall surface of the colon 93 is generated. Then, the image is cut open in parallel to the center line 94 so that an exfoliated image of the inner wall surface of the colon can be displayed as shown in FIG. 14B.

FIGS. 15A to 15E are views for explaining a cylindrical projection method using a cylindrical coordinate system. FIG. 15A shows a cylindrical coordinate system 102 set in the inside of a tubular tissue 101 and a virtual ray 103 radiated from the center axis of the cylindrical coordinate system 102. FIG. 15B shows a state in which the cylindrical coordinate system 102 is represented as $C(h,\alpha)$ based on a distance h along the center axis and an angle $\alpha$ around the center axis. FIG. 15C shows a state in which the cylindrical coordinate $C(h,\alpha)$ is exfoliated and converted into two-dimensional coordinates $l(u,v)$. Each of FIGS. 15D and 15E shows a state in which the virtual ray 103 is radiated from the center axis of the tubular tissue 101. Accordingly, by assuming that a cylindrical coordinate system 102 is set virtually in the inside of a tubular tissue 101 and performing the projection radially from the center axis of the cylindrical coordinate system 102 in this manner, a 360° panoramic image of the inner wall surface of the tubular tissue 101 can be generated.

FIGS. 16A and 16B are views for explaining a curved cylindrical projection method when a tubular tissue as a subject of observation is curved. As shown in FIGS. 16A and 16B, the curved cylindrical projection method is a method of projection in which virtual ray 113 is radiated from a curved center line 112 when the tubular tissue 111 as a subject of observation is curved. As described above, in accordance with the curved cylindrical projection method, by assuming the central path 112 along the real curved internal organ of the human body, and by performing projection with the central path 112 as the center, inspection can be performed with CT data (for example, see "Virtual Colon Unfolding", A. Vilanova Bartroli, R. Wegenkittl, A. Konig and E. Groller, IEEE Visualization, U.S., pp. 411-420, 2001).

In related arts, there is a problem in curved cylindrical projection method when the curve is sharp. When the curve is sharp, virtual rays intersect each other during rendering process, resulting in that some regions of the inner wall surface of the tubular tissue may appear multiple times on the projected image, while other region may not appear at all. Some related arts aim to solve this problem (see "Virtual Colon Unfolding", A. Vilanova Bartroli, R. Wegenkittl, A. Konig and E. Groller, IEEE Visualization, U.S., pp. 411-420, 2001). In order to avoid such a problem, several methods are proposed where virtual rays progress on a curved surface or an oblique plane surface so as not to intersect with each other. However, the curved or plane surface is mathematically differentiable (smooth) at nearby the intersection point of the surface and the central path. Because of this constraint, the virtual rays hardly reach the backside of complex folds.

The above problem cannot be solved by the curved cylindrical projection method in the related art, even when virtual ray is not linear or perpendicular to the central path. In related art, several methods are proposed where virtual ray progress on a curved surface or an oblique plane surface. Those methods are designed to avoid ray intersections. In the curved cylindrical projection method with linear ray casting, virtual rays may intersect with each other at area where the tubular tissue has a large curvature.

Another problem in the curved cylindrical projection method according to the related art is that a region which can be hardly observed is generated depending on the shape of the inner wall surface of the tubular tissue, because the angle of radiation of the virtual ray is fixed, and the virtual ray is radiated in directions perpendicular to the central path.

FIG. 17 is a view for explaining the problem in the curved cylindrical projection method. As shown in FIG. 17, when the inner wall surface of the colon 121 is observed, it is difficult to observe the backside (see the arrow p) of a fold of the colon 121, because virtual ray 123 is radiated in directions perpendicular to the central path 122.

In "Virtual Colon Unfolding", A. Vilanova Bartroli, R. Wegenkittl, A. Konig and E. Groller, IEEE Visualization, U.S., pp. 411-420, 2001, above problem is tried to be solved by a method in which a folded structure of a surface of the target internal organ is unfolded by an approach of finite-element deformation after obtaining the shape of the surface of the target internal organ. However, it is difficult to say that this method is practical, because this method has disadvantages such as that subjective and complex condition setting is necessary in the extraction of the surface of the internal organ, and in the process of unfolding, lesion can not be detected because polyp is also unfolded, and calculation for extracting and unfolding the surface of the internal organ is enormous.

SUMMARY OF THE INVENTION

An object of the present invention is to provide an image processing method and a computer-readable medium by which a shaded portion of an inner wall surface of a tubular tissue can be observed in an objective and simple manner.

An image processing method according to the first aspect of the invention is an image processing method for visualizing information of a living body near an imaginary path which is a center line of a subject of observation, the image processing method comprises determining a ray direction of a virtual ray according to an elevation angle which is an angle between the virtual ray at a ray basis point and a path direction of the path at a ray start point, projecting the virtual ray according to the ray direction passing the ray basis point thereby to generate a projected image, and visualizing the living body information based on the projected image.

According to this configuration, virtual rays progress on a curved or place surface, and at the intersection point of the surface and the path, the surface is undifferentiable (pointed). Accordingly, the virtual rays are radiated onto a shaded portion of the inner wall surface of a tubular tissue having a complex shape, so that the shaded portion, for example polyps hidden by folded inner wall surface of the tubular tissue can be observed.

According to the first aspect of the invention, the image processing method further comprises generating the projected image by volume rendering processing. According to the first aspect of the invention, the image processing method further comprises generating the projected image by surface rendering processing. According to the first aspect of the invention, the image processing method further comprises generating the projected image by network distributed processing. According to the first aspect of the invention, the image processing method further comprises generating the projected image by using a graphics processing unit.

According to the first aspect of the invention, the image processing method further comprises projecting the virtual ray to an inner wall surface of the subject, start points of a plurality of virtual rays being separated and shifted away at a predetermined distance from the path, and the virtual rays being emitted in screw shape.

According to the first aspect of the invention, the image processing method further comprises projecting the virtual ray to an inner wall surface of the subject, the virtual ray being formed in a shape of a curved line or a broken line. According to the first aspect of the invention, the image processing method further comprises projecting the virtual ray spirally to an inner wall surface of the subject. According to the first aspect of the invention, the image processing method further comprises projecting the virtual ray to an inner wall surface of the subject, the virtual ray being formed in vortex-shape.

According to the first aspect of the invention, the image processing method further comprises displaying the projected image simultaneously with an image obtained by a virtual endoscope on a display.

According to the first aspect of the invention, the image processing method further comprises calculating a reflected light of the virtual ray based on a mathematical function including the elevation angle.

According to the first aspect of the invention, the image processing method further comprises changing a calculation step pitch of the virtual ray to be dependent on the elevation angle.

According to the first aspect of the invention, the image processing method further comprises generating a plurality of projected images by dynamically changing the elevation angle. The elevation angle may be changed dynamically by using a graphical user interface, in accordance with a rotation angle around the imaginary path or in accordance with a position on the imaginary path. According to this configuration, because the elevation angle can be changed, the inner wall surface of a tubular tissue can be observed while the elevation angle is changed. Accordingly, all portions including a shaded portion, of the inner wall surface of the tubular tissue can be observed.

According to the first aspect of the invention, the image processing method further comprises displaying the plurality of projected images on a display to be arranged side by side, the plurality of images being different from each other in the elevation angle. According to the first aspect of the invention, the image processing method further comprises displaying an image on a display by synthesizing the plurality of projected images, the plurality of images being different from each other in the elevation angle. According to the first aspect of the invention, the image processing method further comprises displaying the plurality of projected images having different elevation angles in sequential manner.

According to the first aspect of the invention, the image processing method further comprises changing the elevation angle dynamically by using a graphical user interface. According to this configuration, an image favorable to a user can be generated.

According to the first aspect of the invention, the image processing method further comprises changing the elevation angle dynamically in accordance with a rotation angle around the imaginary path. According to this configuration, an optimum image can be generated in accordance with the shape of the tubular tissue.

According to the first aspect of the invention, the image processing method further comprises changing the elevation angle dynamically in accordance with a position on the imaginary path. According to this configuration, an optimum image can be generated in accordance with the shape of the tubular tissue.

According to the first aspect of the invention, the image processing method further comprises calculating a gradient of the projected image on the assumption that each voxel is shear-deformed in accordance with the elevation angle when the projected image is generated based on a voxel data.

A computer-readable medium according to the second aspect of the invention, a computer-readable medium including a processor connected to at least one of an image processing portion, a volume data generating portion, an operating portion and a display device, the processor contains a set of instructions for image processing, the set of instructions comprises determining a ray direction of a virtual ray according to an elevation angle between the virtual ray at a ray basis point and a path direction of the path at a ray start point, projecting the virtual ray according to the ray direction passing the ray basis point to thereby generate a projected image, and visualizing the living body information based on the projected image.

BRIEF DESCRIPTION OF THE DRAWINGS

FIGS. 4A, 4B, 4C and 4D are views for explaining the case where projected images are displayed for the sake of comparison.

FIGS. 6A to 6C are views for explaining gradient calculation in the case where a projected image is generated.

FIGS. 9A and 9B are views for explaining windmill type ray casting.

FIGS. 13A and 13B are views for explaining the parallel projection method and the central projection method respectively.

FIGS. 15A to 15E are views for explaining a cylindrical projection method using a cylindrical coordinate system.

DESCRIPTION OF THE PRFERRED EMBODIMENT

Figure 1:
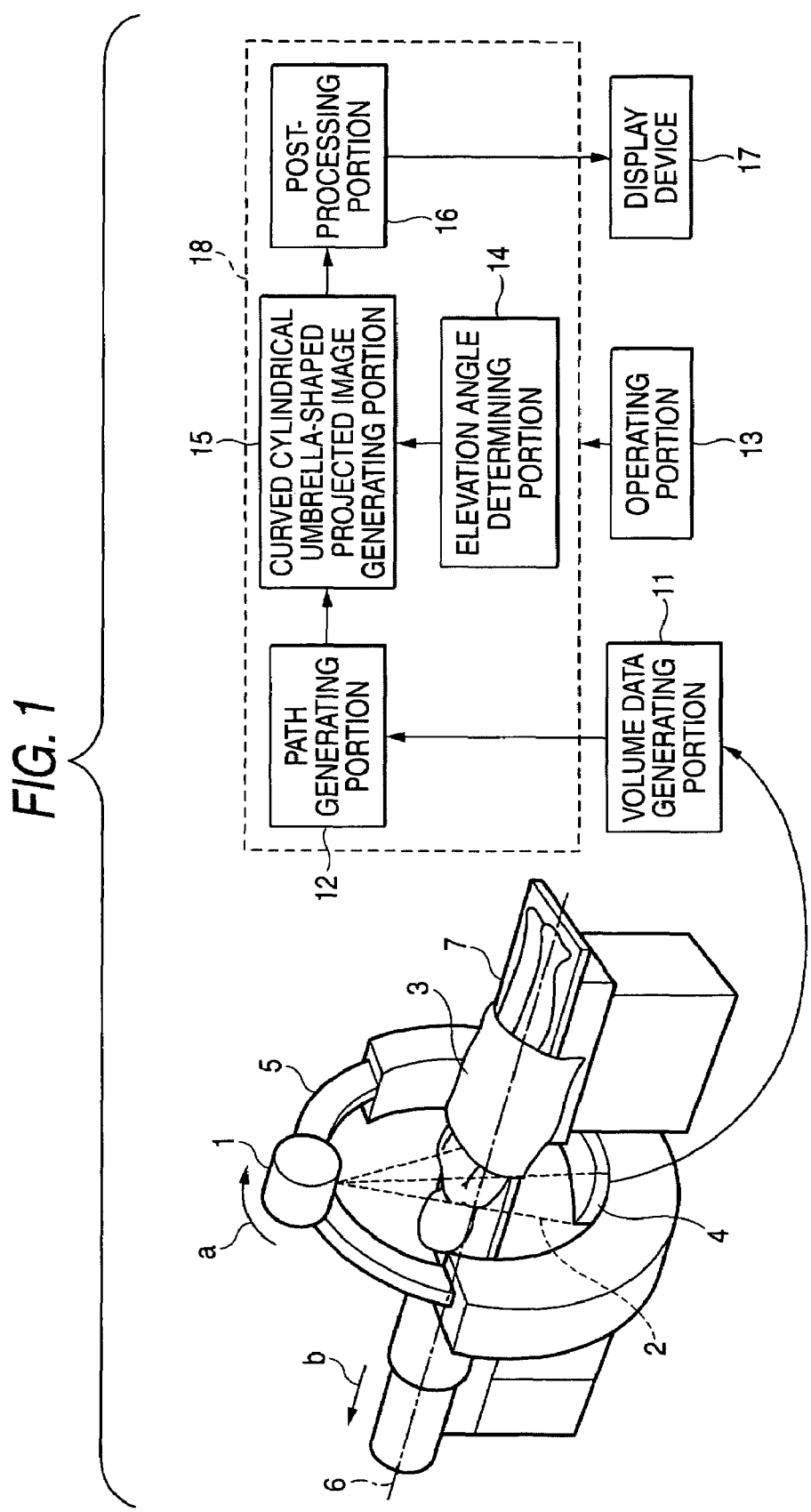
FIG. 1 is a schematic block diagram of a computed tomography using an image processing apparatus according to an embodiment of the invention.

FIG. 1 schematically shows a computed tomography apparatus using an image processing apparatus according to one embodiment of the invention. The computed tomography apparatus is provided for visualizing a tubular tissue or the like of a subject. A pyramid-like X-ray beam 2 having an edge beam represented by the chain lines in FIG. 1 is radiated from an X-ray source 1. The X-ray beam 2 is radiated onto an X-ray detector 4 after being transmitted through the subject, e.g. a patient 3. In this embodiment, the X-ray source 1 and the X-ray detector 4 are disposed in a ring-like gantry 5 so as to face each other. The ring-like gantry 5 is supported by a retainer not shown in FIG. 1 so as to be rotatable (see the arrow "a") about a system axis 6 which passes through the center point of the gantry.

In this embodiment, the patient 3 is lying on a table 7 through which the X-rays are transmitted. The table 7 is supported by a retainer which is not shown in FIG. 1 so as to be movable (see the arrow "b") along the system axis 6.

Thus a measuring system is configured so that the X-ray source 1 and the X-ray detector 4 are rotatable about the system axis 6 and movable along the system axis 6 relatively to the patient 3. Accordingly, X-rays can be cast on the patient 3 at various projection angles and in various positions with respect to the system axis 6. An output signal from the X-ray detector 4 when the X-rays are cast on the patient 3 are supplied to a volume data generating portion 11 and converted into a volume data.

In sequence scanning, the patient 3 is scanned in accordance with each sectional layer of the patient 3. When the patient 3 is scanned, while the X-ray source 1 and the X-ray detector 4 rotate around the patient 3 about the system axis 6 as its center, the measuring system including the X-ray source 1 and the X-ray detector 4 captures a large number of projections to scan each two-dimensional sectional layer of the patient 3. A tomogram displaying the scanned sectional layer is reconstructed from the measured values acquired on that time. While the sectional layers are scanned continuously, the patient 3 is moved along the system axis 6 every time the scanning of one sectional layer is completed. This process is repeated until all sectional layers of interest are captured.

On the other hand, during spiral scanning, the table 7 moves along the direction of the arrow "b" continuously while the measuring system including the X-ray source 1 and the X-ray detector 4 rotates about the system axis 6. That is, the measuring system including the X-ray source 1 and the X-ray detector 4 moves on a spiral track continuously and relatively to the patient 3 until the region of interest of the patient 3 is captured completely. In this embodiment, signals of a large number of successive sectional layers in the abdominal area of the patient 3 are supplied to a volume data generating portion 11 by the computed tomography scanner shown in FIG. 1.

An umbrella-shaped projection method in the image processing method of the present invention will now be described with reference to FIG. 2A. A set of volume data generated by the volume data generating portion 11 is led to a path generating portion 12 in an image processing portion 18. The path generating portion 12 determines a center line of a subject of observation such as a colon (tubular tissue), and generates a path 2a-1 in FIG. 2A along the center line. The path 2a-1 generated by the path generating portion 12 is supplied to a curved cylindrical umbrella-shaped projected image generating portion 15.

On the other hand, an elevation angle determining portion 14 in the image processing portion 18 determines an elevation angle 2a-2 which is an angle between a virtual ray 2a-5 at a ray basis point 2a-3 and a path direction of the path 2a-1 generated by the path generating portion 12 at a ray start point, thereby to determine a ray direction 2a-6 of the virtual ray 2a-5.

The ray basis point and the ray start point according to the invention will now be described with reference to FIG. 2B. A ray basis point b is a point which is the basis of the virtual ray. A ray start point s is a point used in the actual calculation of virtual ray. The ray basis point b may not correspond with the ray start point s because of the condition of the calculation.

Figure 2A:
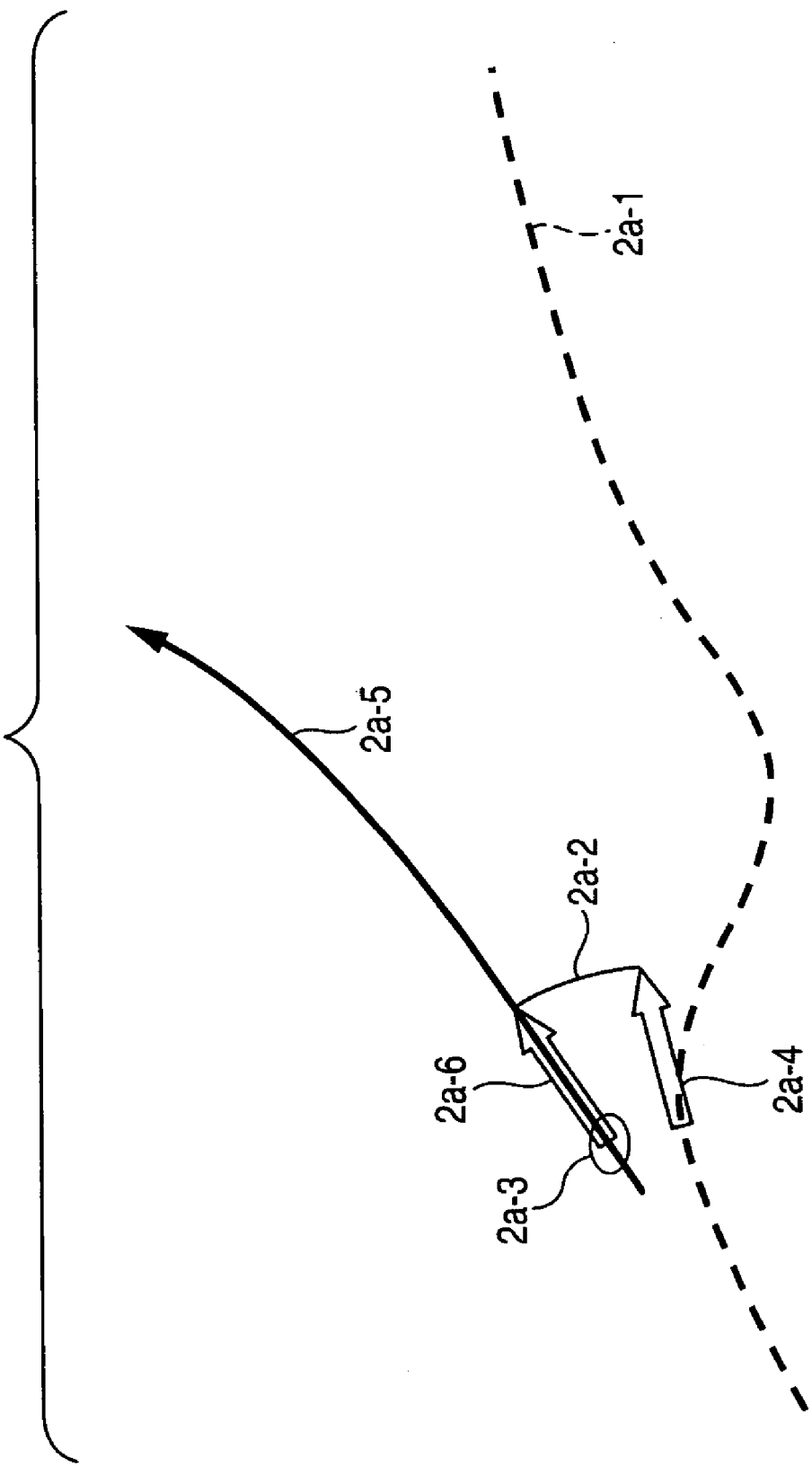
FIGS. 2A, 2B, 2C and 2D are views for explaining an umbrella-shaped projection method in the image processing method according to this embodiment.
Figure 2B:
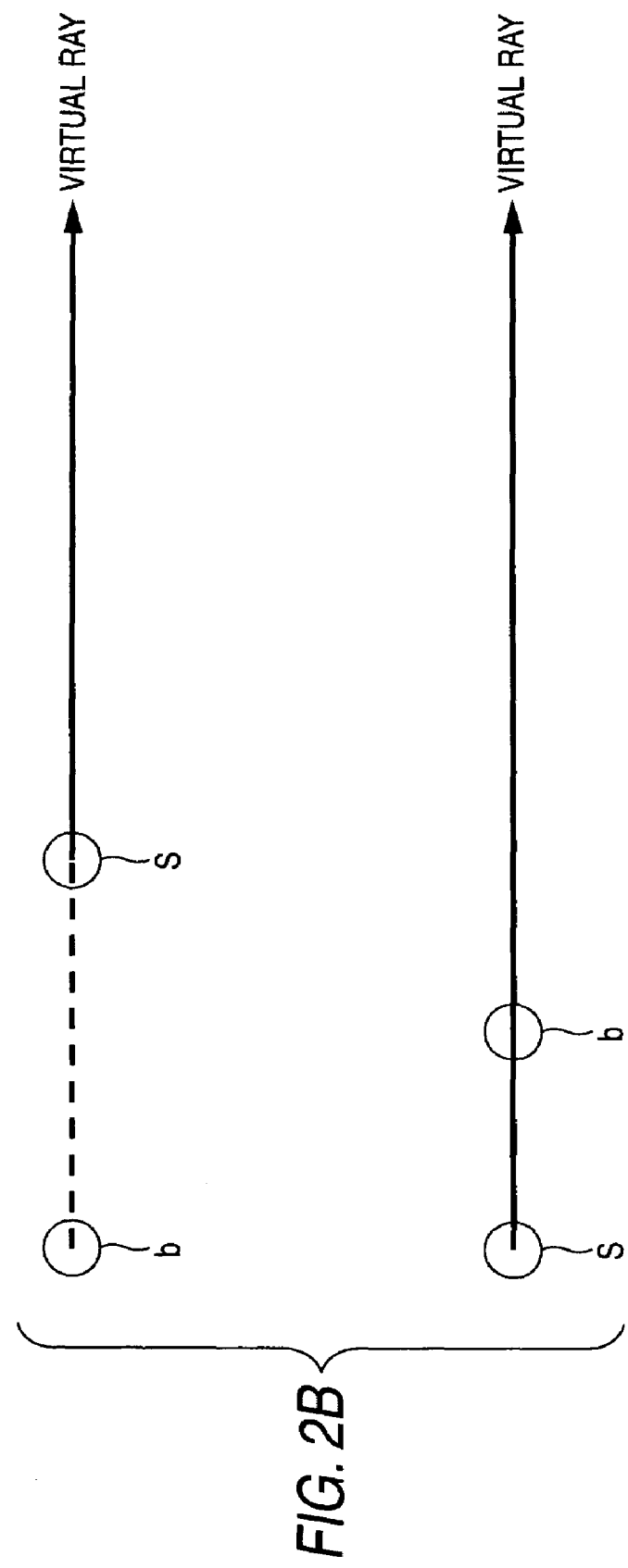

In FIG. 2A, the elevation angle determining portion 14 supplies the elevation angle 2a-2 to the curved cylindrical umbrella-shaped projected image generating portion 15. Incidentally, the elevation angle 2a-2 can be changed interactively by a command given from an operating portion 13 which will be described later.

The curved cylindrical umbrella-shaped projected image generating portion 15 generates a projected image of the tubular tissue by radiating the virtual ray 2a-5 in an umbrella shape in accordance with the elevation angle 2a-2 given from the elevation angle determining portion 14 while moving the ray start point along the path 2a-1 given from the path generating portion 12. The projected image generated in the curved cylindrical umbrella-shaped projected image generating portion 15 is supplied to a post-processing portion 16. The post-processing portion 16 performs processing such as a parallel display of a plurality of projected images each of which corresponds to a different elevation angle, an animation display for successively displaying a plurality of projected images each of which corresponds to a different elevation angle, or a simultaneous display of a projected image and a virtual endoscope (VE) image. The projected image processed in the post-processing portion 16 is supplied to a display device 17 and displayed on the display device 17.

The operating portion 13 generates a control signal such as a signal for changing the elevation angle or a signal for switching the projected image in accordance with an operation signal given from a keyboard, a mouse or the like, and supplies the control signal to the image processing portion 18. Accordingly, a user can change the projected image interactively while watching the projected image displayed on the display device 17, and observe the lesion such as a polyp in detail.

A processor is connected to at least one of an image processing portion 18, a volume data generating portion 11, an operating portion 13 and a display device 17, and controls a system including an image processing portion 18, a volume data generating portion 11, an operating portion 13 and a display device 17.

Figure 2C:
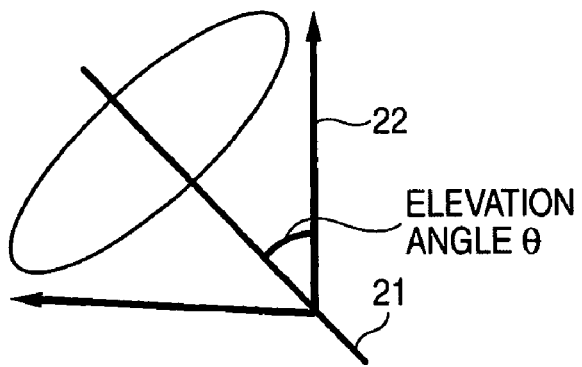
Figure 2D:
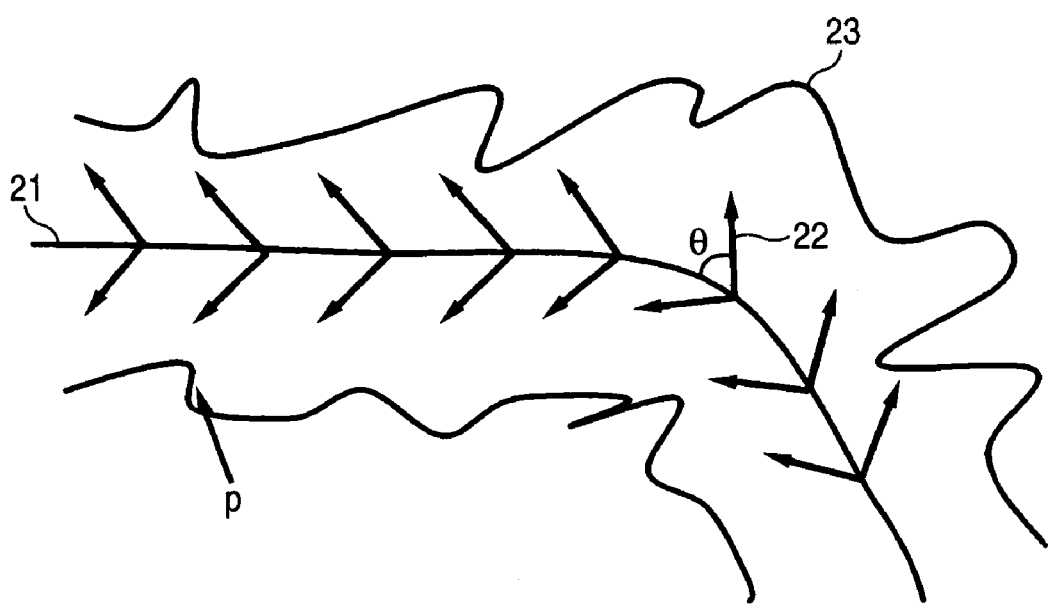

FIGS. 2C and 2D are views for explaining an umbrella-shaped projection method in the image processing method according to this embodiment. As shown in FIG. 2C, in the umbrella-shaped projection method, a virtual ray 22 rotates around the path 21 for 360 degrees while maintaining the direction of the virtual ray 22 to the path 21 at an elevation angle θ, thereby generating a projected image. According to the umbrella-shaped projection method, because the virtual ray 22 is radiated obliquely, a shaded portion (see the arrow p) of the inner wall surface of the tubular tissue 23 can be observed clearly as shown in FIG. 2D.

When the virtual ray 22 rotates around the path 21 for 360 degrees, the elevation angle θ can be changed in accordance with the curve of the path or a command given from the operating portion 13. Because the elevation angle θ can be changed in accordance with the rotation of the virtual ray 22, a projected image of a curved part of the tubular tissue 23 can be corrected so that a projected image without distortion can be generated.

The virtual ray 22 can be radiated linearly or nonlinearly in accordance with a curve of the path or a command given from the operating portion 13. Because the virtual ray 22 can be selectively radiated linearly or nonlinearly, projected image which differs in shading can be generated so that a small polyp or the like can be detected accurately.

Figure 2F:
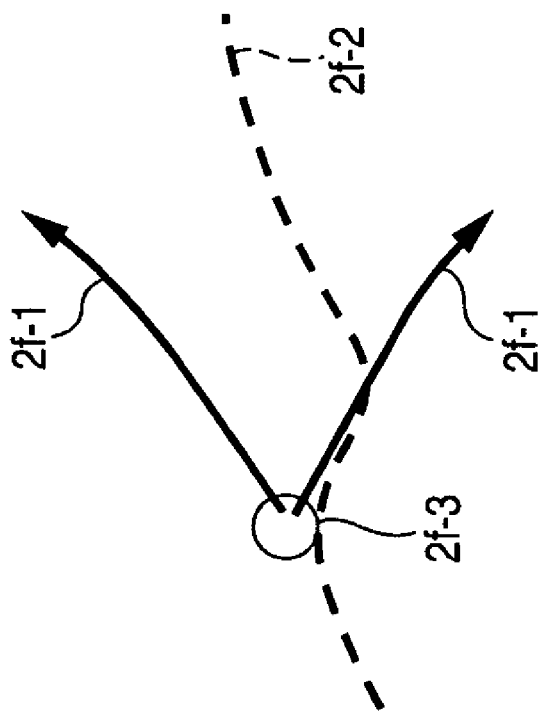
FIGS. 2E and 2F are views for explaining the difference between the umbrella-shaped projection method of the present invention and curved cylindrical projection method of the related art respectively.
Figure 2E:
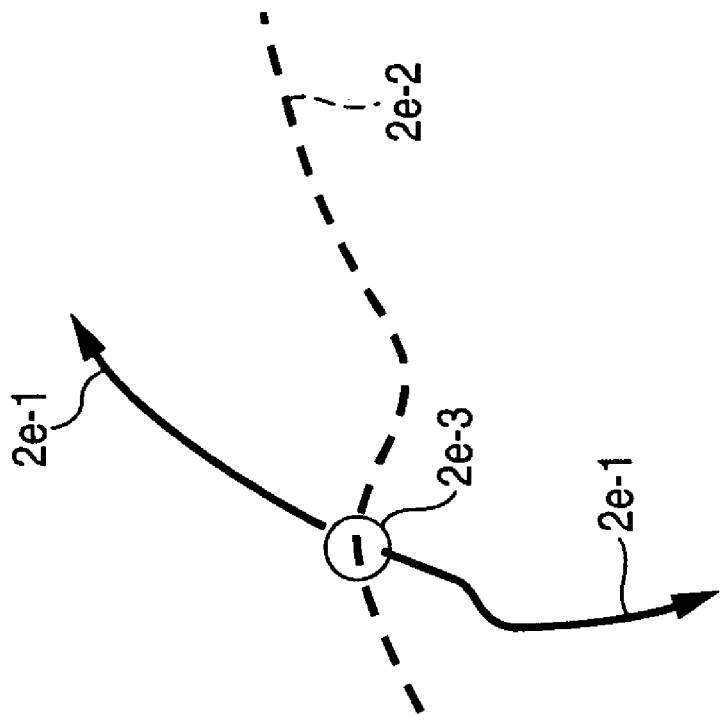

FIGS. 2E and 2F are views for explaining the difference between the umbrella-shaped projection method of the present invention and curved cylindrical projection method of the related art respectively. In the related art, as shown in FIG. 2E, virtual rays 2e-1 travel on a curved or plane surface, and at nearby the intersection point of the surface and a path 2e-2, the surface is mathematically differentiable (smooth). On the other hand, in the umbrella-shaped projection method shown in FIG. 2F, virtual rays 2f-1 also travel on a curved or plane surface, but unlike in the related art, the surface is undifferentiable (pointed) at nearby the intersection point of the surface and a path 2f-2. Accordingly, the virtual rays 2f-1 can effectively radiate onto the inner wall surface of a tubular tissue having a complex shape, thereby generating an image where hidden portion of the inner wall surface, for example, the backside of folds of an inner wall surface of a colon, can be clearly observed. In FIGS. 2E and 2F, ray basis points 2e-3 and 2f-3 are shown respectively.

Figure 3A:
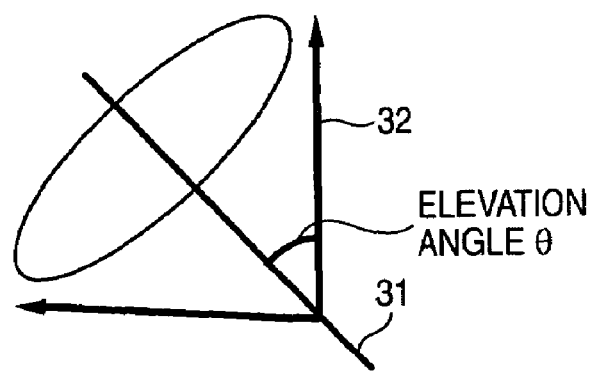
FIGS. 3A and 3B are views for explaining the case where the elevation angle θ is changed to generate a plurality of projected images.
Figure 3B:
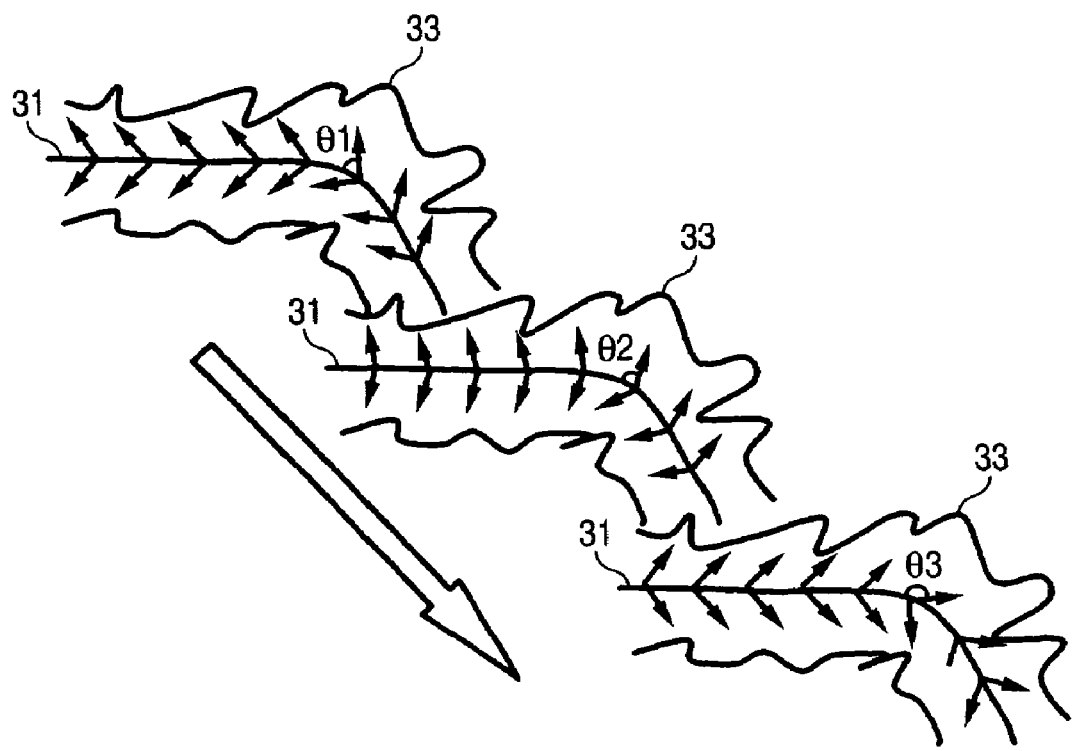

FIGS. 3A and 3B are views for explaining the case where the elevation angle θ is changed to generate a plurality of projected images. As shown in FIG. 3A, in the umbrella-shaped projection method, a virtual ray 32 rotates around the path 31 for 360 degrees at an elevation angle θ, thereby generating a projected image. As described above, the elevation angle θ can be changed by transmitting an operation signal to the operating portion 13 from a keyboard, a mouse or the like. Accordingly, as shown in FIG. 3B, when the elevation angle is changed as θ1, θ2 and θ3, a plurality of projected images can be generated. When the plurality of projected images is compared with one another, a shaded portion of the inner wall surface of the tubular tissue 33 can be observed clearly.

FIGS. 4A, 4B, 4C and 4D are views for explaining the case where the plurality of projected images is displayed for comparison. FIG. 4A shows the case where an observation target 43 on one side of a fold 42 of the tubular tissue 41 is observed. FIGS. 4B, 4C and 4D show the projected images generated by changing each elevation angle θ as 45°, 90° and 135° concerning the same observation target as the observation target 43. In this manner, display of the observation target 43 changes in accordance with the change of the elevation angle θ. Accordingly, change in shape of a lesion can be detected accurately.

Although FIGS. 4B, 4C and 4D show the case where projected images are arranged and displayed, an image synthesized from the projected images different in the elevation angle θ may be displayed. For example, a portion supposed to be a lesion is extracted from the plurality of the projected images different in the elevation angle θ respectively. Then, image processing such as contour emphasis, shading correction, color correction or contrast emphasis is performed on the extracted portions. When an image synthesized from the extracted portions is displayed, progress state of the lesion can be understood accurately. Moreover, when the plurality of the projected images is displayed successively by means of animation display, a slight change in the lesion can be observed clearly.

Figure 5A:
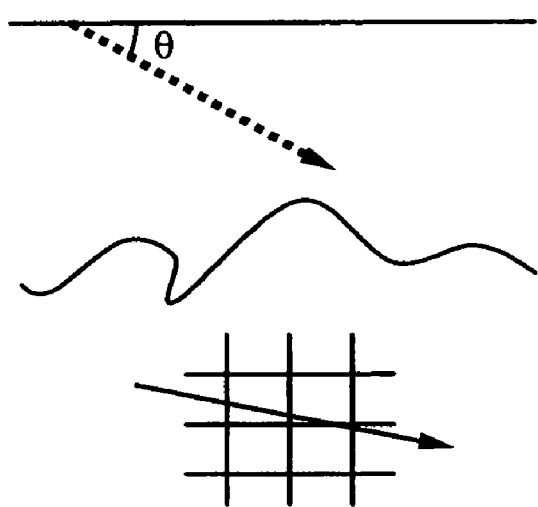
FIGS. 5A and 5B are views for explaining change in ray casting pitch in the case where a virtual ray is cast.
Figure 5B:
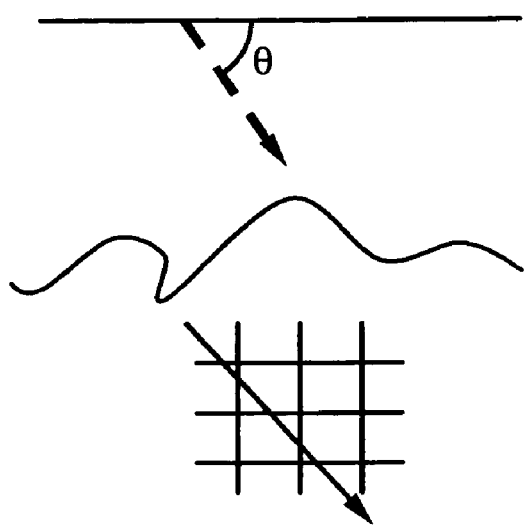

FIGS. 5A and 5B are views for explaining change in ray casting pitch when the virtual ray is radiated. In this embodiment, the pitch for ray casting calculation is changed in accordance with the angle at which the virtual ray is radiated. This is because the crossing angle between the virtual ray and a voxel grid changes according to the radiating angle of the virtual ray. In this manner, projected image distortion in a curved portion can be corrected.

FIGS. 6A to 6C are views for explaining gradient calculation when generating a projected image. When expressing an observation target by a projected image, rather than generating a projected image with the virtual ray 61 obliquely radiated as shown in FIG. 6A, it is preferable to generate a projected image with the observation target being deformed and the virtual ray 63 perpendicularly radiated as shown in FIG. 6B, because reflected light on a surface (see the arrows 62 and 64) of the tubular tissue can be expressed more clearly, and, the target can be understood more intuitively.

However, the deformation of the original volume (observation target) causes increase in calculation amount, increase in use of memory or reduction in image quality. Therefore, for calculation of the reflected light, angle between the virtual ray and a surface is calculated so that the same effect can be obtained. Then, the elevation angle θ of the virtual ray is applied to a gradient function. The gradient is calculated on the assumption that each voxel is shear-deformed in accordance with the elevation angle θ as shown in FIG. 6C. As a result, a projected image with the clear shading can be generated while suppressing the increase in calculation amount.

Figure 7A:
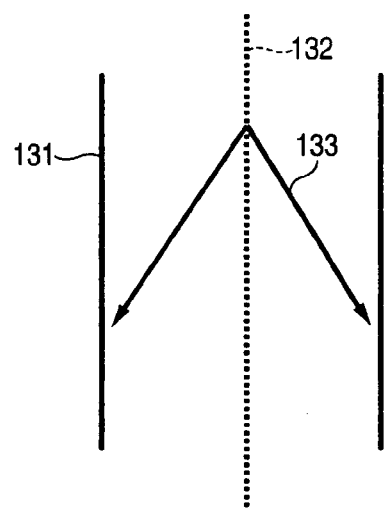
FIGS. 7A and 7B are views for explaining nonlinear ray casting.
Figure 7B:
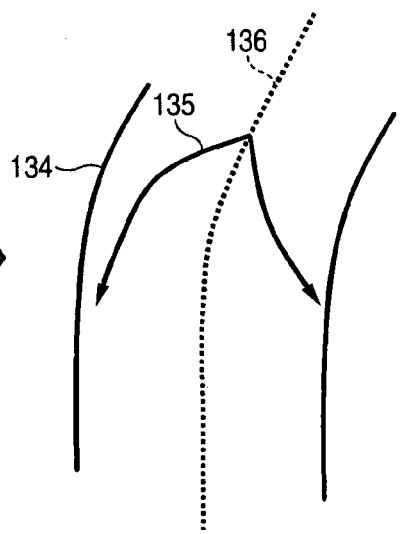

FIGS. 7A and 7B are views for explaining nonlinear ray casting, and show a state in which the tubular tissue is sliced by a plane parallel to the center path. As shown in FIG. 7A, when the tubular tissue 131 is linear, virtual ray 133 is radiated linearly from the center path 132. As shown in FIG. 7B, when the tubular tissue 134 is curved, virtual ray 135 may be conveniently bent in vortex-shape in accordance with the curve of the tubular tissue 134. Alternatively, each virtual ray 135 may be approximated by broken line so that the calculation amount can be reduced.

Figure 8A:
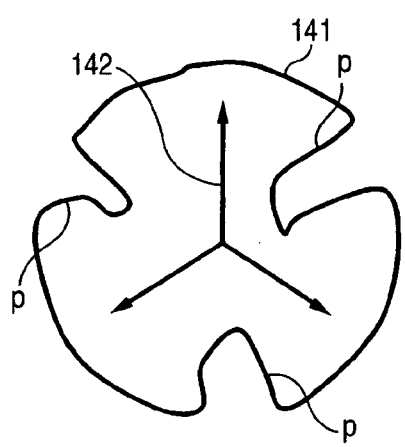
FIGS. 8A and 8B are views for explaining vortex type ray casting.
Figure 8B:
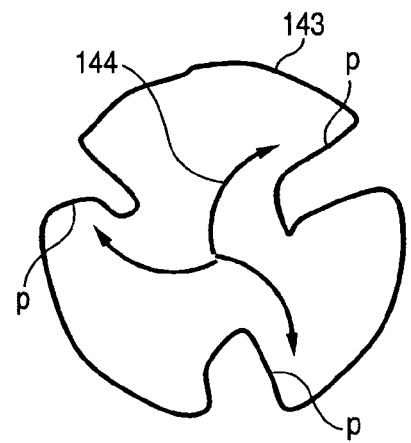

FIGS. 8A and 8B are views also for explaining nonlinear ray casting, and show a state in which the tubular tissue is sliced by a plane perpendicular to the center path. Generally, as shown in FIG. 8A, virtual ray 142 is radiated radially viewing from a section perpendicular to the center path. In this case, folds (see the reference symbol p) along the center path can be sometimes hardly observed.

Therefore, as shown in FIG. 8B, virtual ray 144 is radiated in vortex-shape so as to hit the folds of the tubular tissue 143. As a result, the folds (see the reference symbol p) along the center path can be observed clearly. Also in this case, the calculation amount can be reduced by approximating each virtual ray 144 with broken line.

Both nonlinear ray casting shown in FIG. 7B and nonlinear ray casting shown in FIG. 8B cannot be achieved simultaneously if the virtual ray 144 is radiated in vortex-shape. The two kinds of nonlinear ray casting can be achieved simultaneously when the virtual ray 144 is radiated spirally so as not to stay in an identical plane. Also in this case, the calculation amount can be reduced by approximating each virtual ray 144 with broken line.

FIGS. 9A and 9B are views for explaining windmill-shaped ray casting, and show a state in which the tubular tissue is sliced by a plane perpendicular to the center path. As shown in FIG. 9A, even when the virtual ray 151 is linear, a portion hardly observed by a general casting method can be observed by separating the start point of each virtual ray, and emit virtual ray in screw shape.

FIG. 9B shows an example in which the start point of virtual rays 153 are separated and shifted away from the center path of the tubular tissue 152. Also by this casting method, the folds (see the reference symbol p) along the center path of the tubular tissue 152 can be observed clearly.

Figure 10A:
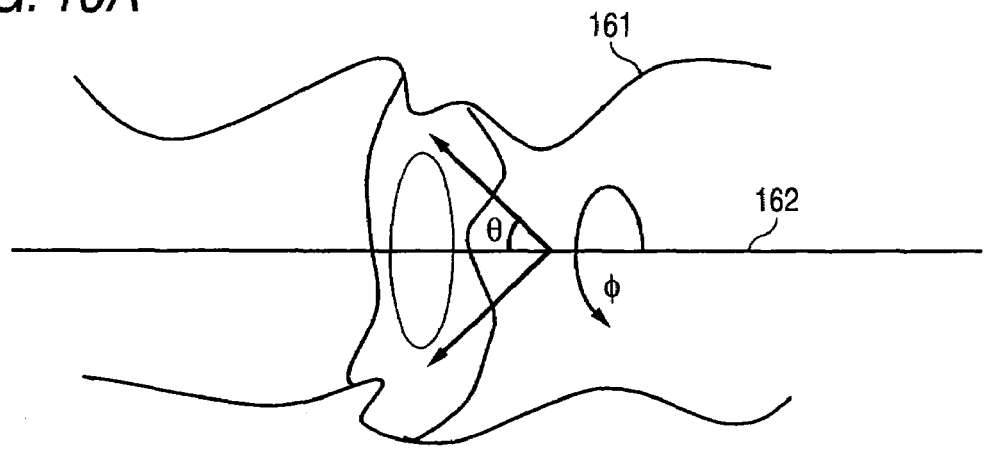
FIGS. 10A to 10C are views for explaining the case where the elevation angle θ is changed according to the angle φ of rotation on the path 162.
Figure 10B:
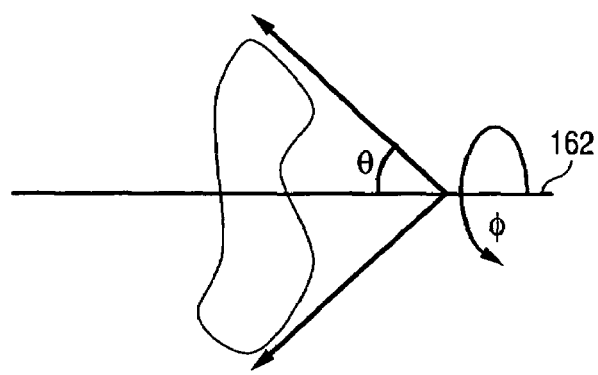
Figure 10C:
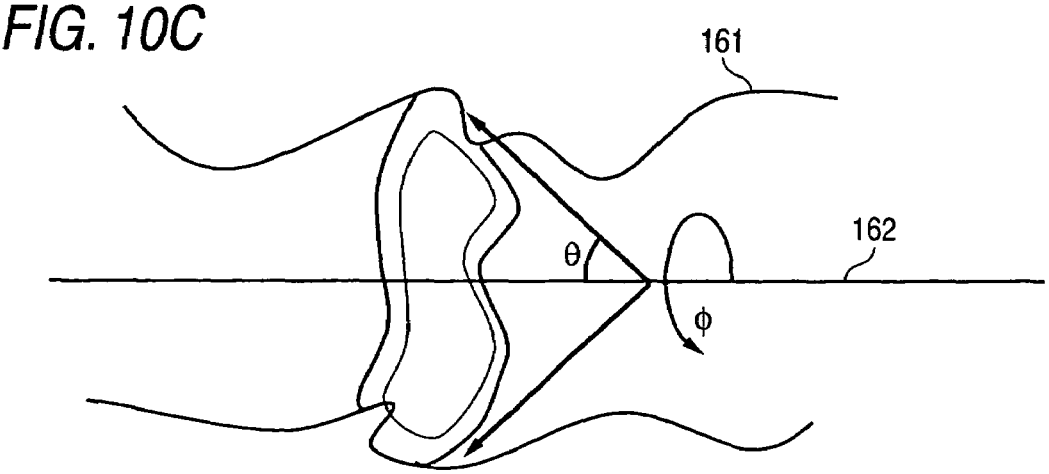

FIGS. 10A to 10C are views for explaining the case where the elevation angle θ is dynamically changed according to the rotation angle φ with path 162 as its axis. That is, in the image processing method according to the embodiment, the elevation angle θ at a ray basis point is constant. The elevation angle θ, however, may be changed dynamically according to the rotation angle φ with the path 162 as its axis. In this case, a set of virtual rays passing the ray basis point can constitute a generalized cone as shown in FIG. 10B, compared with the case where a set of virtual rays passing the ray basis point constitutes a circular cone as shown in FIG. 10A. As a result, the elevation angle θ can be controlled in accordance with the contour of the inner wall surface 161 or the distance between the inner wall surface 161 and the path 162, so that an image can be obtained more clearly (see FIG. 10C).

Figure 11A:
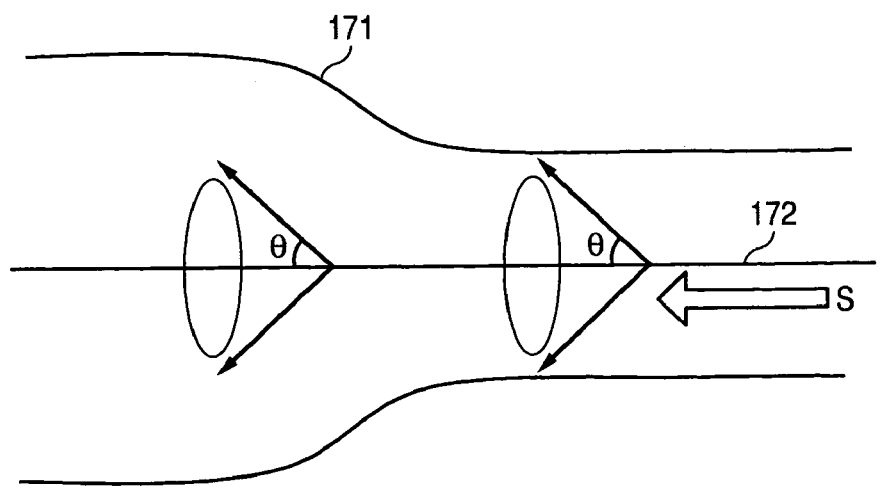
FIGS. 11A to 11C are views for explaining the case where the elevation angle θ is changed according to the position s along the path 172.
Figure 11B:
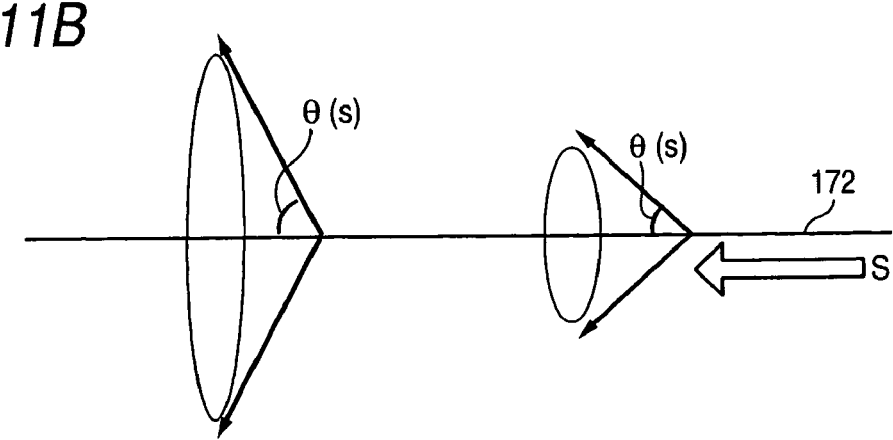
Figure 11C:
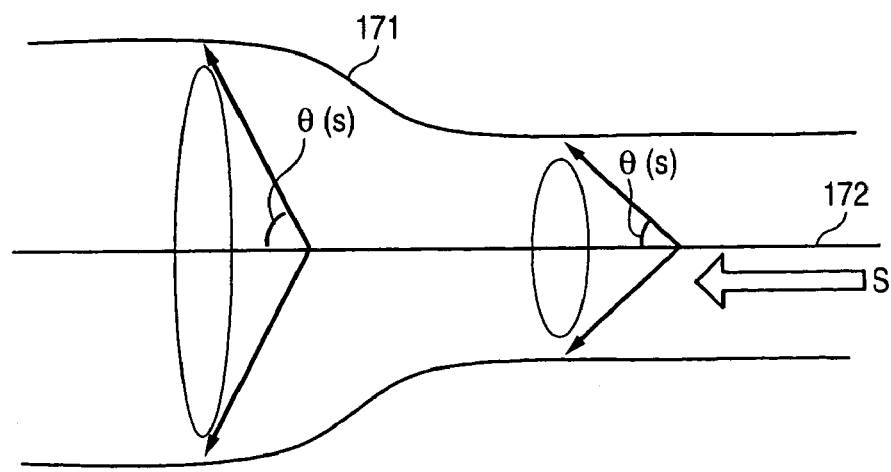
Figure 12A:
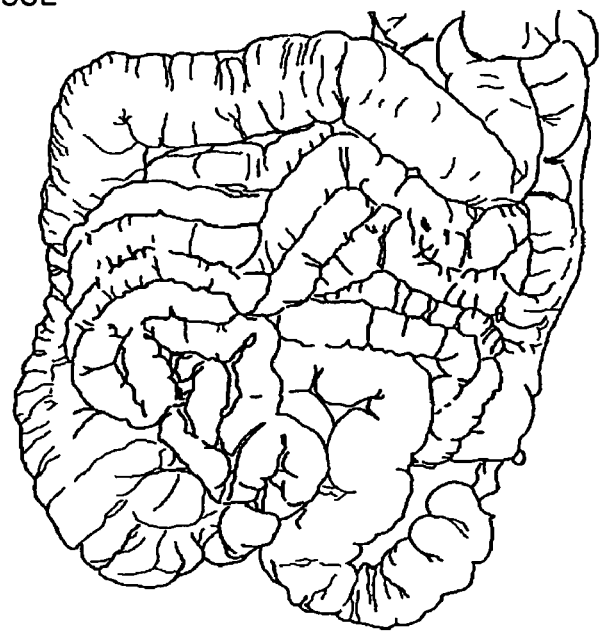
FIGS. 12A and 12B show the case where the colon is displayed by a parallel projection method using volume rendering and the case where the colon is displayed by a central projection method using volume rendering, respectively, as examples of visualization of a tubular tissue in the inside of a human body.
Figure 12B:
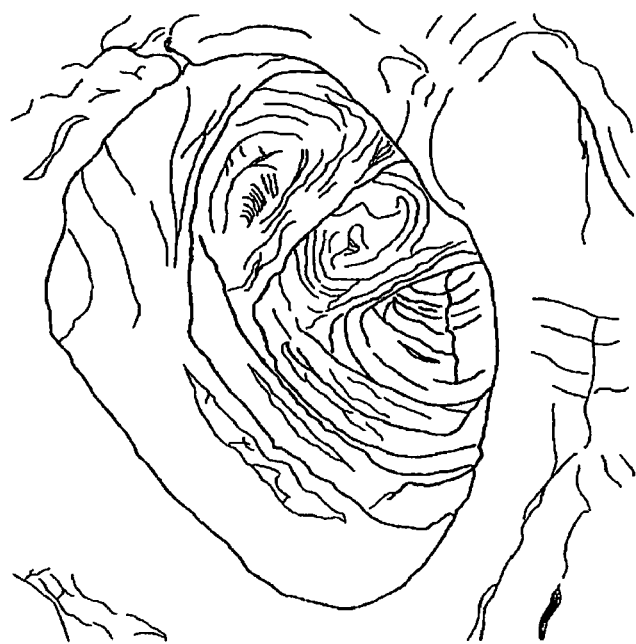
Figure 14A:
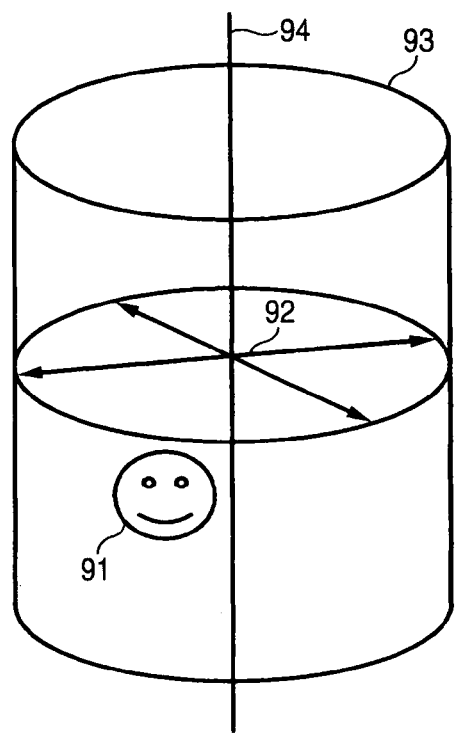
FIGS. 14A and 14B show an example of display of an exfoliated image of a tubular tissue using a cylindrical coordinate system in ray casting.
Figure 14B:
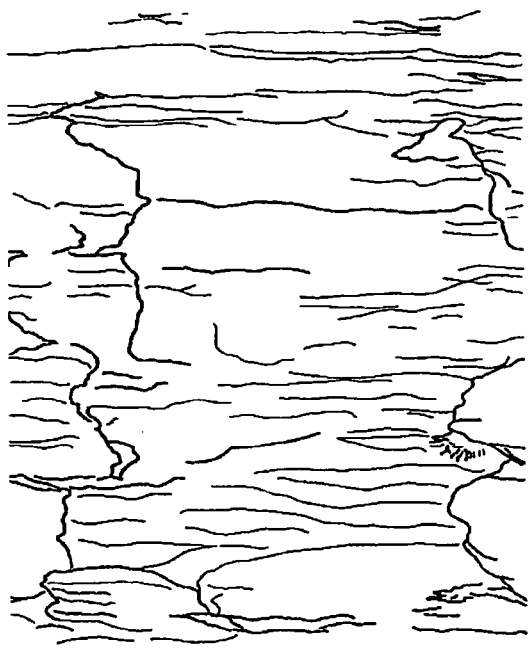
Figure 15C:
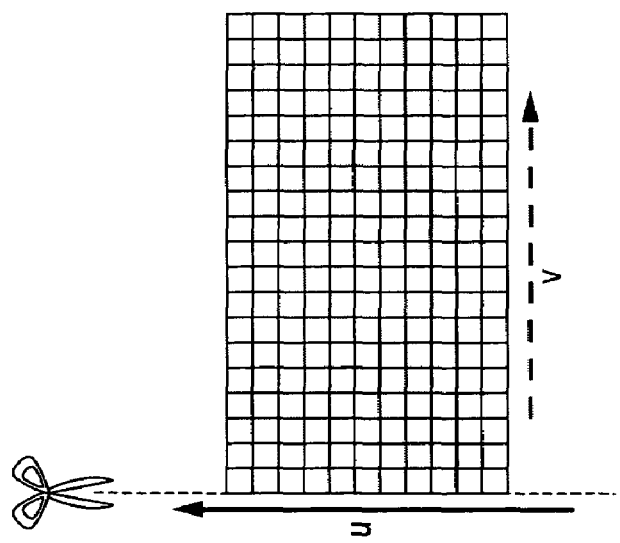
Figure 15B:
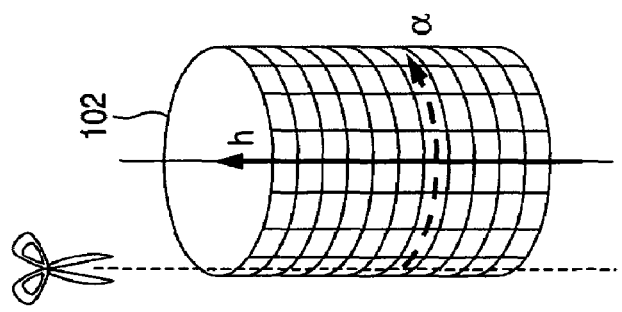
Figure 15A:
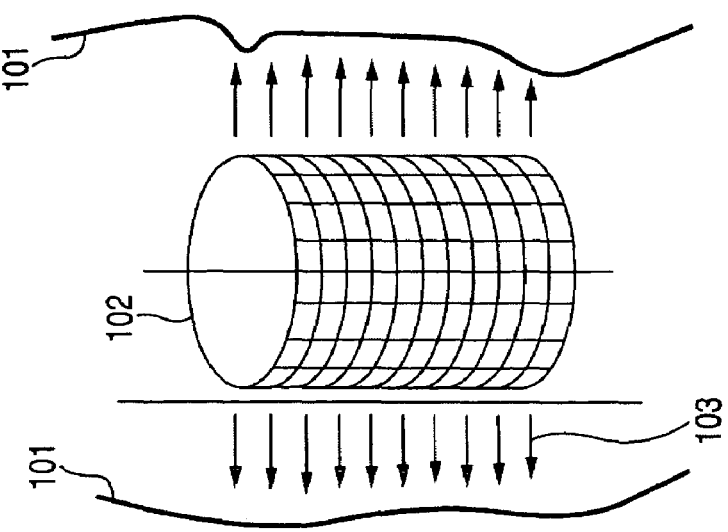
Figure 16A:
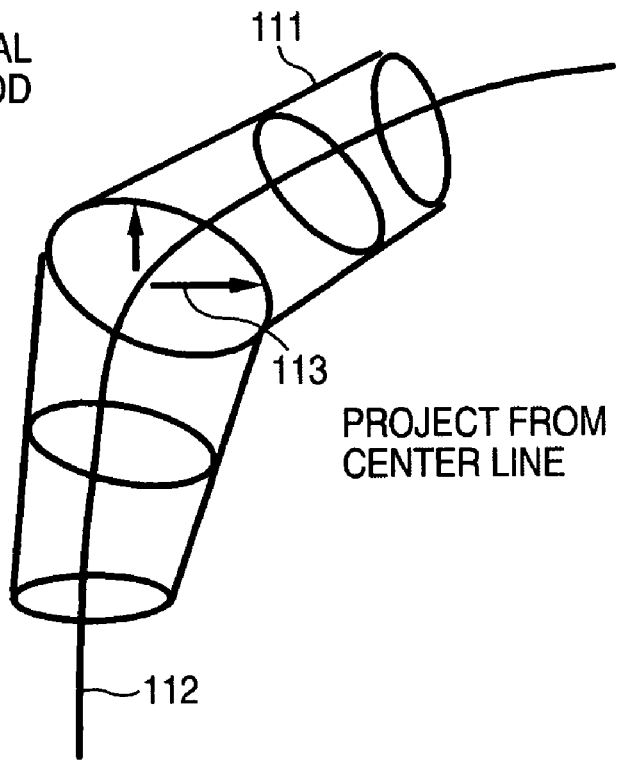
FIGS. 16A and 16B are views for explaining a curved cylindrical projection method in the case where the tubular tissue as a subject of observation is bent.
Figure 16B:
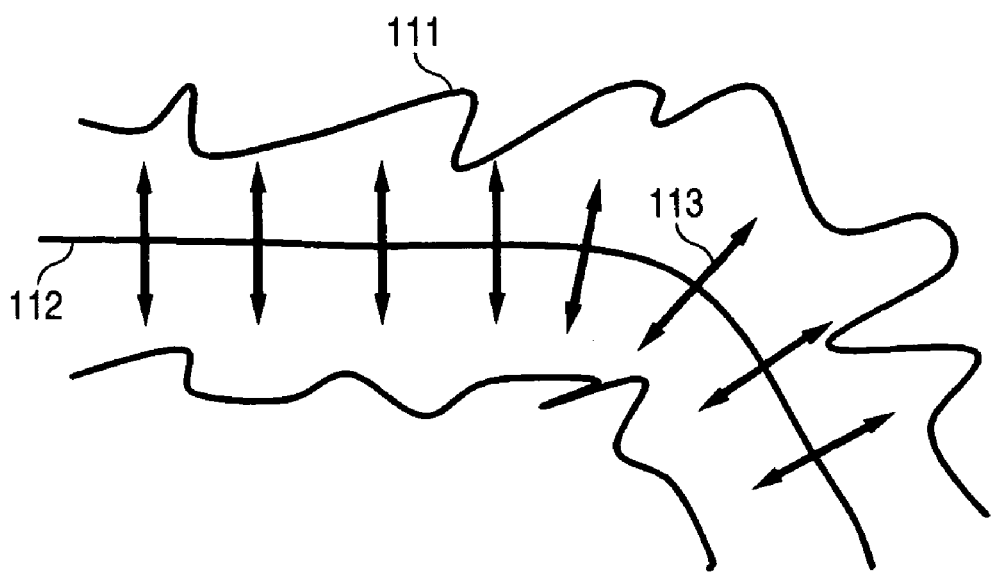
Figure 17:
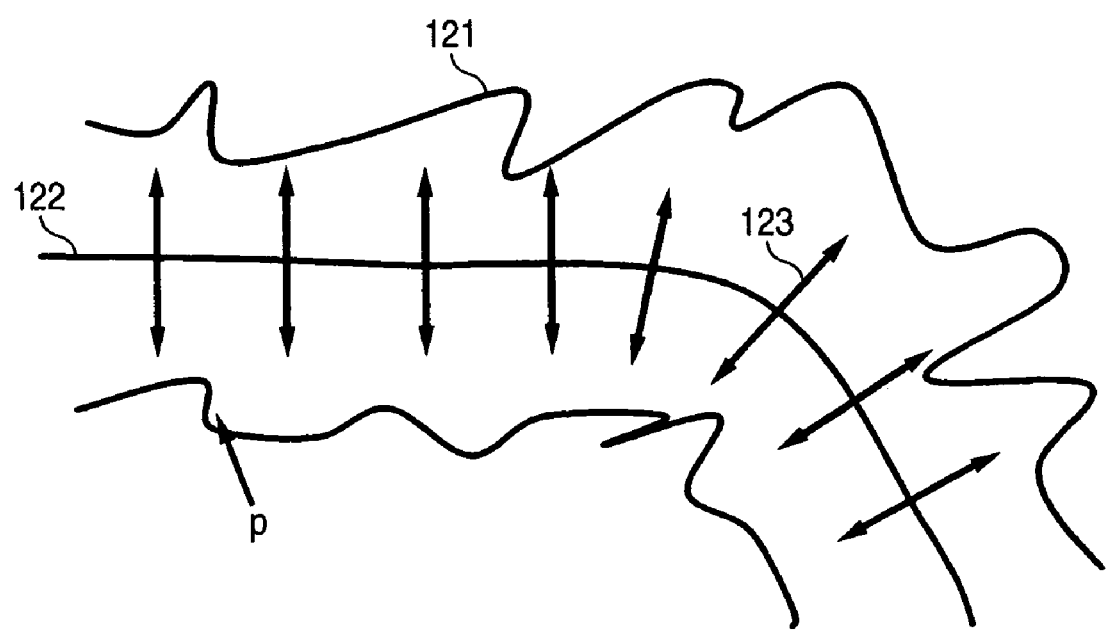
FIG. 17 is a view for explaining a problem in the curved cylindrical projection method.

FIGS. 11A to 11C are views for explaining the case where the elevation angle θ is dynamically changed according to the position s along the path 172. That is, in the image processing method according to the embodiment, the elevation angle θ at a ray basis point is constant (see FIG. 11A). The elevation angle θ, however, may be dynamically changed according to the position s along the path 172 (see FIG. 11B). As a result, the elevation angle θ can be controlled in accordance with the contour of the inner wall surface 171 or the distance between the inner wall surface 171 and the path 172, so that an image can be obtained more clearly (see FIG. 11C).

Incidentally, in the image processing method according to the embodiment, projected image maybe calculated by surface rendering. Surface rendering is a method for visualizing a three-dimensional object by forming a surface data by an element which forms surface such as a polygon as a unit. This method is the same as the image processing method in that virtual ray is used to generate an image. Surface data can be generated from volume data as follows. For example, a suitable threshold is set, the region of volume data is divided into parts, and the boundary plane between the divided regions is obtained.

Incidentally, in the image processing method according to the embodiment, generated image is displayed. However, generated image does not have to be displayed always. This is because in some applications, the generated image may be used by a program or stored for being displayed later.

A calculation process for generating the projected image may be performed by a GPU (Graphics Processing Unit). The GPU is an arithmetic processing unit designed particularly for image processing compared with a general-purpose CPU. Generally, the GPU is mounted in a computer separately from a CPU.

In the image processing method according to this embodiment, calculation for volume rendering can be separated into parts by a predetermined angle unit, a predetermined image region or a predetermined volume region so that the parts can be superposed on one another later. Accordingly, calculation for volume rendering can be performed by parallel processing, network distributed processing, processing in an exclusive processor or a combination of these.

According to the invention, a virtual ray travels on a curved or place surface, and at the intersection point of the surface and the path, the surface is undifferentiable (pointed). Accordingly, the virtual ray is radiated onto a shaded portion such as a portion of the inner wall surface of a tubular tissue having the complex shape, so that the shaded portion of the inner wall surface of the tubular tissue can be observed.

It will be apparent to those skilled in the art that various modifications and variations can be made to the described preferred embodiments of the present invention without departing from the spirit or scope of the invention. Thus, it is intended that the present invention cover all modifications and variations of this invention consistent with the scope of the appended claims and their equivalents.

What is claimed is:

1. An image processing method for visualizing information of a living body near an imaginary path in a subject of observation by using a computer, said image processing method comprising the steps of:
   setting at least two different points along the imaginary path;
   setting a plurality of ray basis points for determining ray directions of virtual rays, each of the plurality of ray basis points corresponding to a different one of said at least two different points along the imaginary path;
   determining the ray direction of each virtual ray according to an elevation angle which is an angle between the virtual ray passing through a ray basis point, and a path direction of said imaginary path;
   projecting at least two different virtual rays according to their respective ray directions while rotating the projected virtual rays around their respective different corresponding points along the imaginary path, thereby to generate a single projected image based on the rotation of the projected virtual rays around said respective different corresponding points along the imaginary path;
   visualizing and displaying on a display device the living body information, based on said single projected image, wherein results of the rotation of the projected virtual rays around said respective different corresponding points along the imaginary path are displayed simultaneously from said single projected image; and
   allowing a user to interactively change the elevation angle.

2. The image processing method according to claim 1, further comprising:
   generating said projected image by volume rendering processing.

3. The image processing method according to claim 1, further comprising:
   generating said projected image by surface rendering processing.

4. The image processing method according to claim 1, further comprising:
   generating said projected image by network distributed processing.

5. The image processing method according to claim 1, further comprising:
   generating said projected image by using a graphics processing unit.

6. The image processing method according to claim 1, further comprising:
   projecting said at least two different virtual rays linearly to an inner wall surface of the subject.

7. The image processing method according to claim 1, further comprising:
   projecting said at least two different virtual rays to an inner wall surface of the subject, start points of a plurality of virtual rays being separated and shifted away at a predetermined distance from the path, and said virtual rays being emitted in screw shape.

8. The image processing method according to claim 1, further comprising:
   projecting said at least two different virtual rays to an inner wall surface of the subject, said virtual rays being formed in a shape of a curved line or a broken line.

9. The image processing method according to claim 8, further comprising:
   projecting said at least two different virtual rays spirally to the inner wall surface of the subject.

10. The image processing method according to claim 8, further comprising:
    projecting said at least two different virtual rays to the inner wall surface of the subject, said virtual rays being formed in vortex-shape.

11. The image processing method according to claim 1, further comprising:
    displaying said projected image simultaneously with an image obtained by a virtual endoscope on a display.

12. The image processing method according to claim 1, further comprising:
    calculating a reflected light of at least one of said at least two different virtual rays based on a mathematical function including said elevation angle.

13. The image processing method according to claim 1, further comprising:
    changing a calculation step pitch of each virtual ray to be dependent on said elevation angle.

14. The image processing method according to claim 1, further comprising:
    generating a plurality of projected images by dynamically changing said elevation angle.

15. The image processing method according to claim 14, further comprising:
    displaying said plurality of projected images to be arranged side by side on the display, said plurality of projected images being differed from each other in said elevation angle.

16. The image processing method according to claim 14, further comprising:

displaying an image on the display by synthesizing said plurality of projected images, said plurality of projected images being differed from each other in said elevation angle.

17. The image processing method according to claim 14, further comprising:
displaying said plurality of projected images having different said elevation angles in sequential manner on the display.

18. The image processing method according to claim 1, further comprising:
changing said elevation angle dynamically by using a graphical user interface.

19. The image processing method according to claim 1, further comprising:
changing said elevation angle dynamically in accordance with a rotation angle around said imaginary path.

20. The image processing method according to claim 1, further comprising:
changing said elevation angle dynamically in accordance with a position on said imaginary path.

21. The image processing method according to claim 1, further comprising:
calculating a gradient of said projected image on the assumption that each voxel is shear-deformed in accordance with said elevation angle when said projected image is generated based on a voxel data.

22. A computer including a processor connected to at least one of an image processing portion, a volume data generating portion, an operating portion and a display device, said processor contains a set of instructions for image processing, said set of instructions comprising:
setting at least two different points along the imaginary path;
setting a plurality of ray basis points for determining ray directions of virtual rays, each of the plurality of ray basis points corresponding to a different one of said at least two different points along the imaginary path;
determining the ray direction of each virtual ray according to an elevation angle which is an angle between the virtual ray passing through a ray basis point, and a path direction of said imaginary path;
projecting at least two different virtual rays according to their respective ray directions while rotating the projected virtual rays around their respective different corresponding points along the imaginary path, thereby to generate a single projected image based on the rotation of the projected virtual rays around said respective different corresponding points along the imaginary path;
visualizing and displaying on the display device living body information, based on said single projected image, wherein results of the rotation of the projected virtual rays around said respective different corresponding points along the imaginary path are displayed simultaneously from said single projected image; and
allowing a user to interactively change the elevation angle.

23. An image processing method for visualizing information of a living body near an imaginary path in a subject of observation by using a computer, said image processing method comprising the steps of:
setting points along the imaginary path;
setting at least one elevation angle between virtual rays and a path direction of said imaginary path;
projecting the virtual rays with said elevation angle while rotating each virtual ray around a different corresponding set point along the imaginary path, thereby to generate a single cylindrical projected image based on the rotation of each projected virtual ray around its different corresponding set point along the imaginary path;
visualizing and displaying on a display device the living body information, based on said single cylindrical projected image, wherein results of the rotation of each projected virtual ray around its different corresponding set point along the imaginary path are displayed simultaneously from said single cylindrical projected image;
allowing a user to interactively change the elevation angle;
projecting the virtual rays with a user-changed elevation angle while rotating each virtual ray around its different corresponding set point along the imaginary path thereby to generate another cylindrical projected image; and
displaying further living body information, based on said another cylindrical projected image.

* * * * *